United States Patent [19]

Yeaple

[11] 4,340,069
[45] Jul. 20, 1982

[54] FORCE-SENSITIVE PROBE AND METHOD OF USE

[75] Inventor: Ronald N. Yeaple, Middlesex, N.Y.

[73] Assignee: Yeaple Corporation, Middlesex, N.Y.

[21] Appl. No.: 85,777

[22] Filed: Oct. 17, 1979

[51] Int. Cl.³ ............................................. A61B 5/10
[52] U.S. Cl. .............................. 128/776; 33/174 D; 433/72
[58] Field of Search ................ 128/776, 774, 777, 1.4; 33/174 D, 169 B, DIG. 1; 433/72

[56] References Cited

U.S. PATENT DOCUMENTS

| | | | |
|---|---|---|---|
| 3,782,188 | 1/1974 | Korber et al. | 128/776 X |
| 3,943,913 | 3/1976 | Johnson | 128/776 |
| 3,943,914 | 3/1976 | Grenfell et al. | 128/776 |
| 4,058,115 | 11/1977 | Forster | 128/776 |

OTHER PUBLICATIONS

Gabathuler et al., "A Pressure Sensitive Peridontal Probe," Helv. Odont Acta, vol. 15, pp. 114-117, Oct. 71.

Velden et al., "Intro. of a New Peridontal Probe . . . ," J. Clin. Peridon, 1978:5, 188-197.

Vitel et al., "Development of a Force Controlled . . . Instr.," J. Periodontal Res, 14: 93-94, 1979.

Primary Examiner—Lee S. Cohen
Attorney, Agent, or Firm—Cumpston & Shaw

[57] ABSTRACT

The object of the invention is to provide a pressure responsive probe and method of use for manually applying a predetermined probing force to an object such as the floor of a periodontal pocket, for example.

The probe has a magnetizable member 28, and a movable lever 14 having a probe tip 18 at one end. The lever 14 and member 28 have cooperating surfaces 24, 30 respectively. The member 28 is magnetized for holding lever 14 in a normally "engaged" position in which the surfaces 24, 30 are held engaged with a preset magnetic force. When a predetermined probing force manually applied to the floor of a periodontal pocket through probe tip 18 overcomes the preset magnetic force, the lever 14 is moved to a "disengaged" position in which the surfaces 24, 30 are disengaged. The depth of the pocket can be observed on a scale on the probe tip at the predetermined probing force.

28 Claims, 8 Drawing Figures

FORCE-SENSITIVE PROBE AND METHOD OF USE

DESCRIPTION

1. Technical Field

This invention relates to probes, and more particularly to a force-sensitive probe and method for manually applying a predetermined probing force to an object such as the floor of a periodontal pocket, for example.

A periodontal probe is a widely used diagnostic tool for the clinical assessment of periodontitis. The probe is used for measuring the depth of periodontal pockets surrounding a tooth, and the loss of connective tissue attached to a floor surface. In investigations designed to measure the probing force manually applied by clinicians to the tip of the periodontal probe, the forces measured ranged from 3 to 130 grams. This large variation of probing force produces major errors in pocket depth measurement. In one clinical study of the relationship between probing force and measured pocket depth, it was found that pockets measured with 50 grams of probing force averaged 56% deeper than those measured with 15 grams of probing force. Accordingly, if pocket depths are to be measured accurately, a periodontal probe and method of application is needed which precisely indicates and standardizes the probing force manually applied to the floor of the pocket.

2. Background Art

A pressure-sensitive periodontal probe is described in an article entitled "A Pressure-Sensitive Periodontal Probe" by H. Gabathuler and T. Hassell (1971). In this probe, a piezo-electric pressure-sensitive sensor is mounted above the probe tip, and the probing force is transferred from the tip to the sensor by a piston mounted within bushings in the probe neck. Voltages generated within the sensor as a result of manually applied forces exerted on the probe tip are led through a shielded cable to a charge amplifier and from there to a dynagraph writer. One disadvantage of this probe and its complex electronic circuitry is the inherent drift in the system which affects the accuracy of the probing force manually applied to the floor of a periodontal pocket. For this reason, the measuring time per pocket must be short, and is limited by a foot pedal assembly to 3 seconds.

Another pressure-sensitive periodontal probe is described in an article entitled "Microscopic Evaluation of Clinical Measurements of Connective Tissue Attachment Levels" by Armitage, Svanberg and Löe (1977). In this probe, a needle shaft is reciprocally mounted within a transparent cylinder, and a delicate spring is interposed between the cylinder and the needle shaft to which a probe tip is secured at one end. When a probing force is manually applied to the probe tip, the opposite end of the needle shaft is moved within the transparent cylinder against the bias of the spring and into alignment with a pressure mark on the cylinder indicating that a predetermined force is being applied to the probe tip. One disadvantage of this probe is that its accuracy is affected by (1) the internal sliding friction of its moving parts, and (2) the lack of precision and stability of the delicate spring.

Still another pressure-sensitive probe is disclosed in an article entitled "Introduction of a New Periodontal Probe: the Pressure Probe" by Vandervelden and DeVries (1978). The pressure probe comprises a metal tube within which a metal plunger is reciprocally mounted. The plunger is connected by a wire to a piston within the handle of the probe. The piston is connected to an air pressure source for applying a predetermined force to the plunger. When the manually applied probing force exceeds the predetermined force, the plunger and piston are moved inwardly, and such inward movement is readable on a scale. A disadvantage of this probe is that its accuracy and stability is affected by the internal friction between the sliding parts, and the difficulty in maintaining a precise source of air pressure.

U.S. Pat. No. 3,943,914 discloses a remote-recording periodontal depth probe for the simultaneous measurement and remote recordation of the depth of a periodontal pocket. A disadvantage of this probe is that no means are incorporated therein or disclosed for measuring or controlling the probing force manually applied to the probe tip.

DISCLOSURE OF THE INVENTION

In accordance with the present invention, a force responsive probe is disclosed for manually applying a predetermined probing force to an object such as the floor of a periodontal pocket, for example. In addition, the probe can be used for measuring the depth of the pocket at the predetermined probing force. The probe comprises a magnetizable member mounted within the probe body. A movable lever is also mounted within the body and has a probe tip insertable into a periodontal pocket. The lever has a portion thereof formed from a magnetic material and is further movable between an "engaged" position in which the lever portion is attracted to and engages the member, and a "disengaged" position in which the lever portion is disengaged from the magnetizable member. The probe also comprises means for magnetizing the magnetizable member for releasably holding the lever in its "engaged" position with a preset magnetic force. In this position, the probe is adapted to be inserted into a periodontal pocket and a manual probing force applied thereto when the end of the probe engages the floor of the pocket. When the probing force is increased to the predetermined probing force value, it overcomes the preset magnetic force generated by the magnetizing means causing the lever portion to be moved to its "disengaged" position. The depth of the pocket can then be observed and read on a depth measuring scale on the probe tip for the predetermined probing force.

In a more specific aspect of the invention, the lever is pivotally mounted for movement between its "engaged" and "disengaged" positions. The lever has a probe tip transverse to one end thereof onto which is scribed a depth measuring scale and further has a beveled surface portion at the opposite end thereof formed from the magnetic material. The member is fixed in axial alignment with the lever, and has a beveled surface at one end thereof parallel to and facing the beveled surface on the lever. In one embodiment, the magnetizing means comprises an electrical coil encircling the member, and a power control source separate from but electrically connected to the probe by an electrical cord for energizing the coil. In another embodiment, the magnetizing means comprises a permanent magnet which is adjustably movable into and out of engagement with the member for varying the predetermined magnetic force. This eliminates the need for a power control source separate from the probe.

Also in accordance with the present invention, a method is disclosed for manually applying a predetermined probing force to the floor of a periodontal pocket with a pressure-sensitive periodontal probe, and for measuring the depth of the pocket at the predetermined probing force. The method comprises the step of magnetically holding the tip of the probe with a predetermined magnetic force in an "engaged" position relative to the probe for insertion of the tip into a periodontal pocket. While in the "engaged" position, the probe tip is then slid along a tooth into the pocket until the end of the tip engages the floor of the pocket. An increasing manual force is applied to the probe urging the tip against the floor until a predetermined probing force is achieved which overcomes the preset magnetic force causing the tip to move from its "engaged" position to a "disengaged" position relative to the probe. The operator then reads the depth of the periodontal pocket on the probe tip scale at the predetermined probing force.

In a further aspect of the method invention, the movement of the probe tip to its "disengaged" position is sensed, and in response thereto an annunciator is actuated.

The force-responsive probe and method for applying a predetermined probing force to the floor of a periodontal pocket and measuring the depth of the pocket possesses the advantage that the probing force can be controlled with great accuracy and stability. Other advantages of the probe are that it (1) has a range of sensitivity from 5 to 100 grams of probing force, (2) can be preset to register at any force within this range, (3) is not sensitive to lateral forces, (4) is not subject to errors due to gravity, (5) has virtually no internal friction to cause errors, (6) is light-weight and rugged, and (7) in prolonged clinical usage for a period of many months, has maintained its preset accuracy to within plus or minus one gram.

BRIEF DESCRIPTION OF THE DRAWINGS

The details of this invention will be described in connection with the accompanying drawings, in which.

BEST MODES FOR CARRYING OUT THE INVENTION

Figure 1:
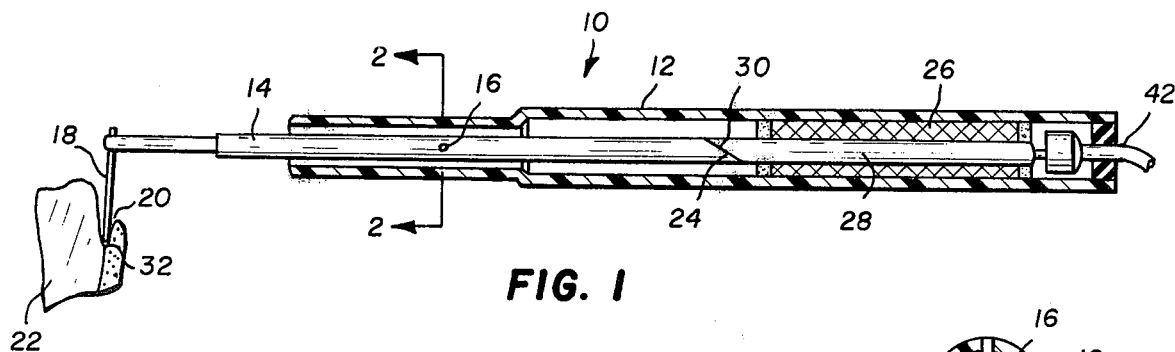
FIG. 1 is a side elevational view of the probe partially in section with the movable lever thereof in its "engaged" position.
Figure 2:
FIG. 2 is a section view taken substantially along line 2—2 of FIG. 1.

With reference to FIGS. 1 and 2, a periodontal probe 10 constructed in accordance with this invention comprises a unitary cylindrical body or tube 12 having one end preferably of a smaller diameter than the opposite end. The body may also be formed by inserting an end of a first tube into an end of another tube having an inner diameter slightly larger than the outside diameter of the first tube. The tube ends are secured together by adhesive or any other suitable means.

A lever 14 is mounted within the smaller end of body 12 for pivotal movement about a pivot pin 16 extending through the lever and through opposite sides of the body. One end of lever 14 is provided with a preferably removable tip 18 formed out of metal or plastic. The tip 18 is inclined at an angle substantially 10° from the vertical to facilitate insertion of the tip into a periodontal pocket 20 adjacent a tooth 22. The opposite end of lever 14 has a beveled surface 24 and is formed of magnetic material. The pivot pin 16 is located at the center of gravity of the lever so that the accuracy of the probe is not affected by gravitational forces.

A coil 26 having an outer diameter substantially equal to the inner diameter of the larger end of body 12 is mounted within the larger end of the body and is secured thereto by any suitable means. The coil 26 encircles and is secured to a magnetizable member 28 such as a core formed out of magnetizable material such as iron. The core member 28 has one end extending outwardly from the coil, and such end is provided with a beveled surface 30 adjacent beveled surface 24 on lever 14.

Figure 3:
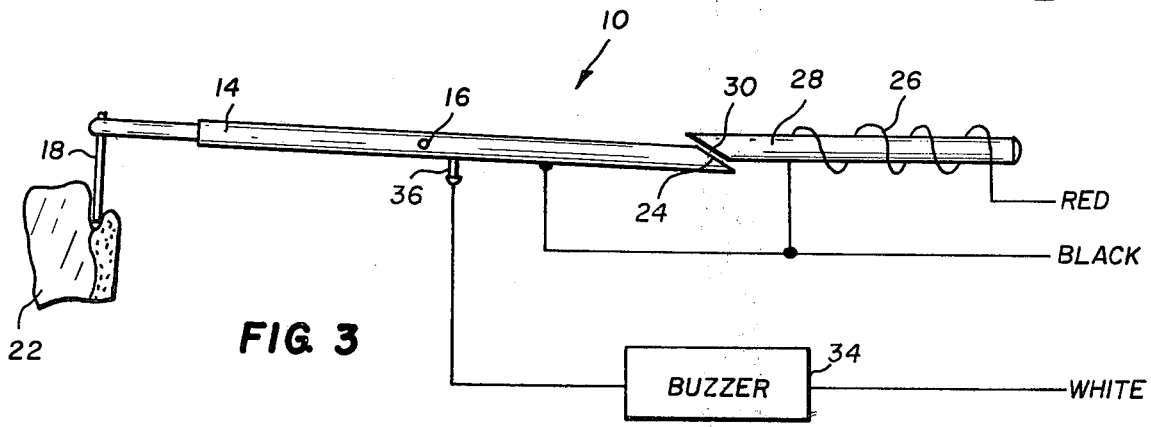
FIG. 3 is a fragmentary side elevational view of the probe with portions thereof omitted for purposes of clarity, and showing the movable lever in its "disengaged" position.

When coil 26 is energized by introducing current therethrough, core member 28 is magnetized for attracting beveled end 24 of lever 14 and releasably holding the lever in an "engaged" position as seen in FIG. 1. In this "engaged" position, the probe 10 is in condition for use wherein the probe tip 18 can be inserted into a periodontal pocket into engagement with the floor 32 thereof, and manual force of increasing value applied thereto. When a predetermined probing force is reached, such force overcomes or exceeds the magnetic force produced by coil 26 causing the lever to pivot into a "disengaged" position as seen in FIG. 3 for breaking the magnetic connection between the two beveled surfaces 24, 30. When this occurs, the operator can read the depth of the periodontal pocket 20 which occurs at this predetermined probing force.

With reference to FIG. 3, a sensing means including an annunciator 34 is disclosed for indicating to the operator that lever 14 has been moved to its "disengaged" position. This is achieved by providing an electrical metallic contact 36 secured to body 12 and engageable by the metallic end of the lever. The annunciator 34 which may comprise a lamp, buzzer or the like has one electrical lead connected to the metallic end of lever 14 and another lead connected to a power source. Accordingly, when lever 14 is moved to its "disengaged" position, the lever end engages electrical contact 36 completing the electrical circuit to the annunciator. This visually or audibly indicates to the operator that the manually applied probing force has overcome the magnetic force produced by coil 26.

Figure 4:
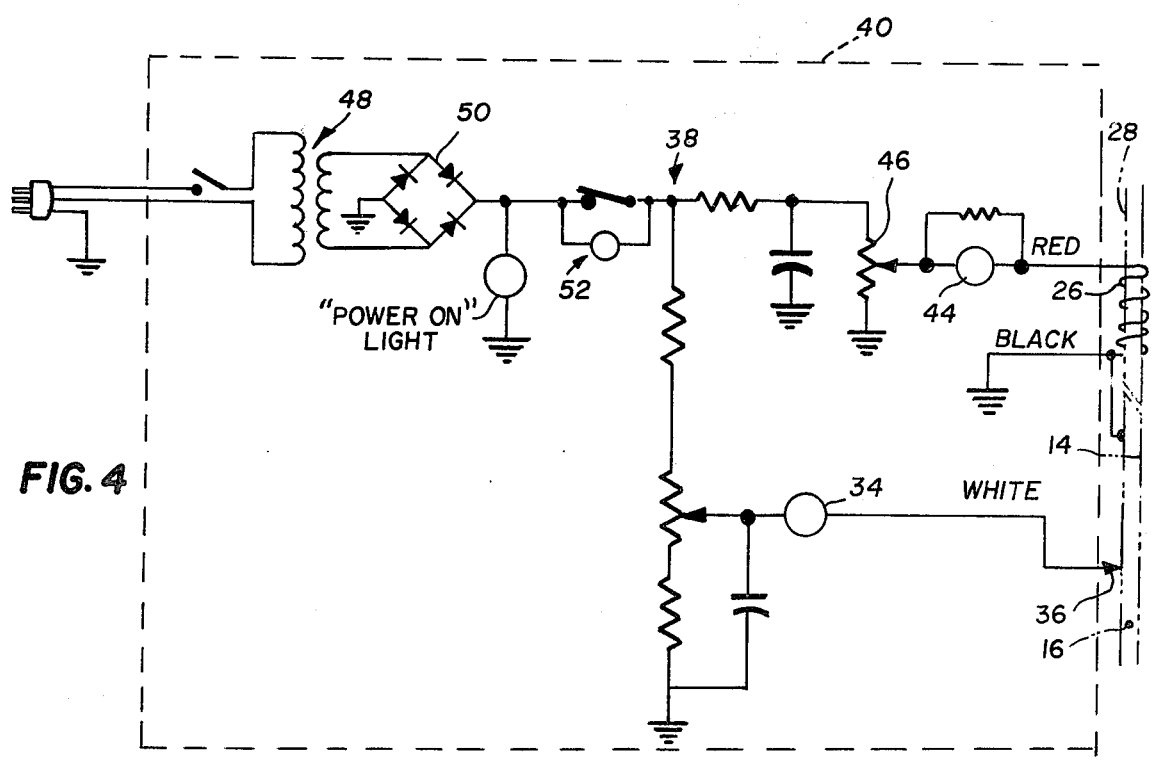
FIG. 4 is an electrical wiring diagram of the electrical control system for the probe.

The magnetic force of the coil is variable for selectively setting the probe to subject the floor 32 of a pocket 20 to manually applied predetermined probing forces ranging from 5 grams to 100 grams. This is achieved by any suitable electrical control circuit 38 such as that shown in FIG. 4 mounted within a control box, shown as a dotted box 40. The probe 10 is connected to box 40 by an extensible electrical cord 42. The current passing through coil 26 is read on a meter 44 mounted on the face of the control box, and is varied by slidably moving a rheostat 46 or the like by a knob on the box.

The electrical circuit 38 is provided with known components such as a step down transformer 48 for reducing the voltage from 120 volts to substantially 12 volts, and a full wave rectifier 50 for converting the alternating current to direct current. By the use of suitable resistors, including rheostat 46, the voltage across the coil within the probe body can be varied within a voltage range not to exceed 2 volts for varying the current therethrough for generating varied magnetic forces. A scale is normally provided to correlate the meter current readings with the grams of predetermined manually applied probing force sensitivity at probe tip 18.

The probe 10 and control circuit 38 are calibrated by using a laboratory balance to apply a predetermined amount of probing force in grams to the probe tip. The current control knob is adjusted and the amount of current through coil 26 observed on meter 44 at the point where lever 14 moves to its "disengaged" position. Accordingly, the meter reading at such point can thereafter be used to accurately adjust the probe to subject the floor 32 of a periodontal pocket 20 to a manually applied probing force equal to the predetermined probing force.

The electrical control circuit 38 is further provided with a demagnetizer 52 for removing the residual magnetism from the probe. The demagnetizer should be actuated for approximately one second each time the magnetic force is adjusted. No force should be applied to the probe tip 18 during demagnetization to insure that the beveled surfaces 24, 30 will be closed and demagnetized.

Figure 5:
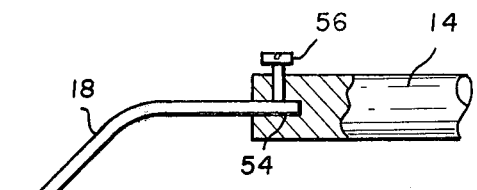
FIG. 5 is a side elevational view partially in section showing one embodiment of a tip holder for the probe.
Figure 6:
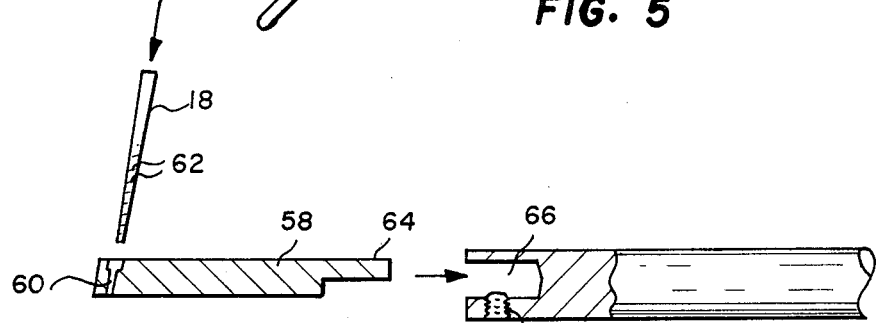
FIG. 6 is a view similar to FIG. 5 showing another embodiment of the tip holder.

With reference to FIGS. 5 and 6, various ways are disclosed for removably securing standard metal or pre-sterilized disposable plastic tips 18, either straight or hook-shaped, to the lever end. In FIG. 5, the probe tip 18 is formed as a hook-shaped member having one end insertable into a complementary opening 54 in lever 14, and secured thereto by a set screw 56. In FIG. 6 a probe tip holder 58 is provided having a stepped hole 60 inclined at an angle of substantially 10° to the vertical for receiving a slim conical tip provided with a scribed measuring scale 62 in millimeters. The probe tip 18 is inserted into the hole and pressed downwardly until the tip wedges into the hole. The tip holder 58 has a flange 64 at the opposite end insertable into a complementary recess 66 in core member 28, and is secured thereto by a set screw 68 or the like. A plurality of tip holders 58 can be provided with each probe, with each holder drilled to accept a different size tip 18.

Figure 7:
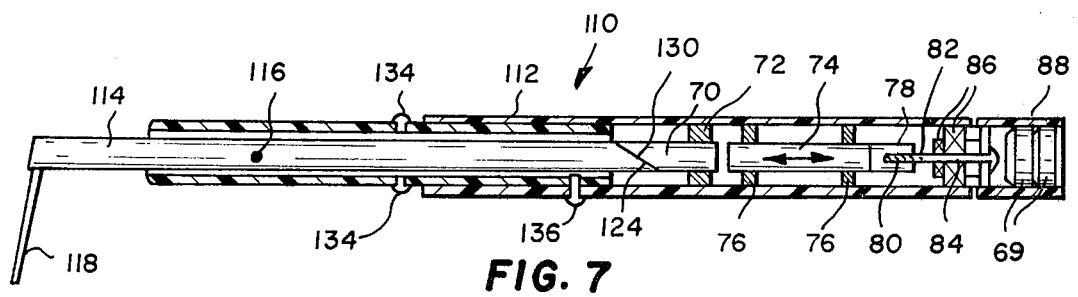
FIG. 7 is a side elevational view similar to FIG. 1 showing another embodiment of the probe of this invention.
Figure 8:
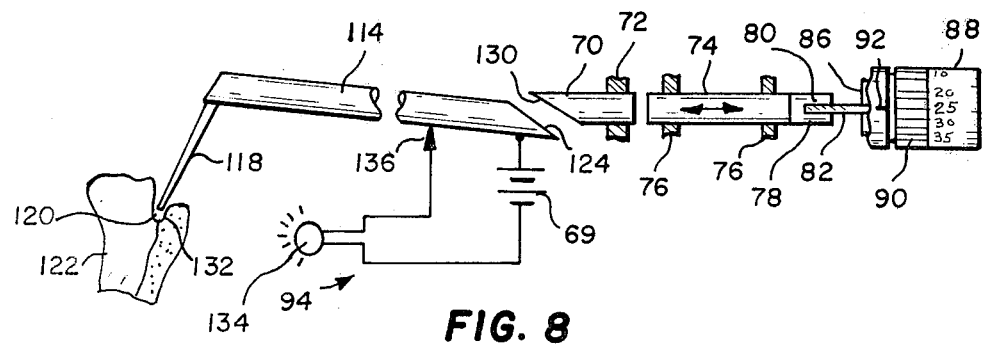
FIG. 8 is a side elevational view similar to FIG. 3 showing the movable lever in its "disengaged" position.

With reference to FIGS. 7 and 8, another embodiment of the invention is disclosed in which parts similar to parts disclosed in the first embodiment are designated by the same numeral plus 100. In this embodiment, the power supply comprises one or more batteries 69 mounted in a cavity in the probe itself thereby eliminating the need for a separate power supply, electrical control circuit and connecting cord. A member 70 such as a rod of magnetizable material is rigidly secured to body 112 by a mounting 72. The rod member 70 has a beveled surface 130 adjacent to and facing beveled surface 124 on lever 114. The probe 110 further has a permanent magnet 74 comprising a rod preferably of square cross section mounted for slidable movement within mountings 76 fixed to probe body 112. A cylinder 78 of nonmagnetic material is secured by adhesive or the like to the end of magnet 74 in axial alignment therewith, and has a threaded bore 80 for receiving the threaded end 82 of a stub shaft 84. The shaft is mounted for rotation within a suitable bearing 86 and the opposite end thereof secured to a cylindrical knob 88. Upon rotation of the knob, shaft 84 is rotated causing threads 82 at the end thereof to move cylinder 78 and permanent magnet 74 toward and away from magnetic rod member 70 for changing the magnetic force with which the rod member attracts the end of lever 114. A scale 90 is provided on the outer periphery of the knob which is movable into alignment with an index 92 on body 112 for indicating the amount of manually applied probing force required to overcome the magnetic force generated by rod member 70 at that setting.

The annunciator means 94 for the probe comprises a plurality of light emitting diode indicators 134 mounted on body 112, as well as an electrical contact 136 on the body spaced from and engageable by a metallic portion of lever 114. The light emitting diodes 134, contact 136 and batteries 69 within knob 88 are electrically connected together as schematically indicated in FIG. 8 such that the electrical circuit is broken and the light emitting diodes are not lit when lever 114 and magnetized rod member 70 are in their "engaged" position as best seen in FIG. 7. However, when the probing force manually applied to tip 118, within pocket 120 overcomes the magnetic force, the lever is moved to its "disengaged" position as seen in FIG. 8 in which beveled surface 124 of the lever is disengaged from beveled surface 130 of magnetized rod member 70. In this "disengaged" position lever 114 engages contact 136 completing the electrical circuit to light emitting diodes 134. The diodes light up visually indicating to the operator that the predetermined probing force manually applied to the floor 132 of periodontal pocket 120 is equal to the force in grams indicated on knob scale 90 opposite index mark 92.

Although in the preferred modes of operation, the levers 14, 114 and members 28, 70 are arranged in aligned relation, it is, of course, possible for them to be arranged in some other suitable orientation, such as at an angle to one another. In such event, one or both of the interengaging surfaces 24, 30 and 124, 130 could be flat rather than beveled. For example, if the lever and member were arranged at right angles to one another, the interengaging surfaces could both be wholly beveled or flat, or each surface could consist of a combination of beveled and flat portions.

The invention has been described in detail with particular reference to preferred embodiments thereof, but it will be understood that variations and modifications can be effected within the spirit and scope of the invention as described.

What is claimed is:

1. A force responsive periodontal probe for manually applying a predetermined probing force to the floor of a periodontal pocket, and for measuring the depth of the pocket when said predetermined probing force is applied, comprising:
   a probe body;
   a magnetizable member mounted within said body;
   a movable lever mounted within said body and having a probe tip extending from said body which is insertable into the periodontal pocket, said probe tip having a periodontal pocket depth measuring scale placed thereon, said lever having a portion thereof formed from a magnetic material, and said lever further being movable between an engaged position in which said lever portion engages said member, and a disengaged position in which said lever portion is disengaged from said member; and means for magnetizing said magnetizable member for attracting and releasably holding said lever portion in said engaged position with a preset magnetic force whereby when said probe tip is moved into engagement with the floor of the pocket, and the probing force, manually applied through said body and said probe tip to the floor of the pocket, is increased to said predetermined probing force, said preset magnetic force is overcome causing said lever to move relative to said body from said engaged position to said disengaged position whereupon the depth of said pocket can be observed on said scale on said probe tip at said predetermined probing force.

2. The probe according to claim 1 wherein said lever is pivotally mounted for pivotal movement between said engaged and disengaged positions.

3. The probe according to claim 1 wherein said magnetizable member is fixedly mounted.

4. The probe according to claim 1 wherein said magnetizing means comprises an electrical coil encircling a part of said magnetizable member, and a power source electrically connected to said coil for energizing said coil.

5. The probe according to claim 1 wherein said lever is pivotally mounted for pivotal movement between said engaged and disengaged positions, said magnetizable member is fixedly mounted, and said magnetizing means comprises an electrical coil encircling said member, and a power source electrically connected to said coil for energizing said coil.

6. The probe according to claim 1, and further having sensing means connected to said lever for sensing movement of said lever to said disengaged position for indicating to the operator that said predetermined probing force is applied to the floor of the periodontal pocket.

7. The probe according to claim 6 wherein said sensing means comprises a visual indicator.

8. The probe according to claim 6 wherein said sensing means comprises an audible indicator.

9. The probe according to claim 1 wherein said lever is pivotally mounted for movement between said engaged and disengaged positions, and said probe tip extends transverse to one end of said lever, said lever portion has a beveled surface, said magnetizable member is fixedly mounted and positioned in axial alignment with said lever and has a beveled surface at one end thereof parallel to and facing said beveled surface on said lever portion, and said magnetizing means comprises an electrical coil encircling said member, and a power source electrically connected to said coil for energizing said coil.

10. The probe according to claim 1 wherein said magnetizing means comprises a permanent magnet.

11. The probe according to claim 10 wherein means are provided for adjustably moving said permanent magnet into and out of engagement with said magnetizable member for varying said preset magnetic force.

12. The probe according to claim 1 wherein said lever is pivotally mounted for movement between said engaged and disengaged positions, and said probe tip extends transverse to one end of said lever, said lever portion has a beveled surface, said magnetizable member is fixedly mounted and positioned in axial alignment with said lever and has a beveled surface at one end thereof parallel to and facing said beveled surface on said lever portion, and said magnetizing means comprises a permanent magnet, and means for adjustably moving said permanent magnet into and out of engagement with said magnetizable member for varying said preset magnetic force.

13. A method for manually applying a predetermined probing force to the floor of a periodontal pocket with a force sensitive periodontal probe, and for measuring the depth of the pocket on a scale on said probe when said predetermined probe force is applied, comprising the steps of:
   (a) magnetically holding with a preset magnetic force the tip of a periodontal probe in an engaged position relative to the probe for insertion of the probe tip into the periodontal pocket;
   (b) sliding the probe tip while in the engaged position along a tooth surface into the periodontal pocket until the end of the probe tip engages the floor of the pocket;
   (c) applying an increasing probing force to the probe tip against the floor until the probing force reaches said predetermined probing force wherein it overcomes said preset magnetic force causing the tip to move from said engaged position to a disengaged position relative to the probe; and
   (d) determining the depth of the periodontal pocket from the scale on the probe at said predetermined probing force.

14. The method according to claim 13 comprising the added steps of sensing movement of the probe tip to the disengaged position, and actuating an annunciator when such movement occurs for indicating to the operator that said predetermined probing force is being applied to the floor of the pocket.

15. A method for manually applying a predetermined probing force to an object such as the root of a gum pocket with a force sensitive probe, comprising the steps of:
   (a) magnetically holding the tip of a probe in an engaged position relative to the probe with a preset magnetic force;
   (b) placing the probe tip while in the engaged position against the object; and
   (c) applying an increasing probing force to the probe tip against the object until the probing force reaches said predetermined probing force wherein it overcomes said preset magnetic force causing the tip to move from said engaged position to a disengaged position relative to the probe indicating that said predetermined probing force is being applied to the object.

16. The method according to claim 15 comprising the added steps of sensing movement of the probe tip to the disengaged position, and actuating an annunciator when such movement occurs for indicating to the operator that said predetermined probing force is being applied to the object.

17. A pressure responsive probe for manually applying a predetermined probing force to an object such as the root of a gum pocket, comprising:
   (a) a probe body;
   (b) a magnetizable member mounted within said body;
   (c) a movable lever mounted within said body and having a probe tip extending from said body which is engageable with the object, said lever having a portion thereof formed from a magnetic material, and said lever further being movable between an engaged position in which said lever portion engages said member, and a disengaged position in which said lever portion is disengaged from said member; and (d) means for magnetizing said magnetizable member for attracting and releasably holding said lever portion in said engaged position with a preset magnetic force whereby when said probe tip is moved into engagement with the object, and the probing force manually applied through said body and said probe tip to the object is increased to said predetermined probing force, said preset magnetic force is overcome causing said lever to move relative to said body from said engaged position to said disengaged position indicating that said predetermined probing force is being manually applied to the object.

18. The probe according to claim 17 wherein said lever is pivotally mounted for pivotal movement between said engaged and disengaged positions.

19. The probe according to claim 17 wherein said magnetizable member is fixedly mounted.

20. The probe according to claim 17 wherein said magnetizing means comprises an electrical coil encircling a part of said magnetizable member, and a power source electrically connected to said coil for energizing said coil.

21. The probe according to claim 17 wherein said lever is pivotally mounted for pivotal movement between said engaged and disengaged positions, said magnetizable member is fixedly mounted, and said magnetizing means comprises an electrical coil encircling said member, and a power source electrically connected to said coil for energizing said coil.

22. The probe according to claim 17, and further having sensing means connected to said lever for sensing movement of said lever to said disengaged position for indicating to the operator that said predetermined probing force is applied to the object.

23. The probe according to claim 22 wherein said sensing means comprises a lamp.

24. The probe according to claim 22 wherein said sensing means comprises a buzzer.

25. The probe according to claim 17 wherein said lever is pivotally mounted for movement between said engaged and disengaged positions, and said probe tip extends transverse to one end of said lever, said lever portion has a beveled surface, said magnetizable member is fixedly mounted and positioned in axial alignment with said lever and has a beveled surface at one end thereof parallel to and facing said beveled surface on said lever portion, and said magnetizing means comprises an electrical coil encircling said member, and a power source electrically connected to said coil for energizing said coil.

26. The probe according to claim 17 wherein said magnetizing means comprises a permanent magnet.

27. The probe according to claim 26 wherein means are provided for adjustably moving said permanent magnet into and out of engagement with said magnetizable member for varying said preset magnetic force.

28. The probe according to claim 17 wherein said lever is pivotally mounted for movement between said engaged and disengaged positions, and said probe tip extends transverse to one end of said lever, said lever portion has a beveled surface, said magnetizable member is fixedly mounted and positioned in axial alignment with said lever and has a beveled surface at one end thereof parallel to and facing said beveled surface on said lever portion, and said magnetizing means comprises a permanent magnet, and means for adjustably moving said permanent magnet into and out of engagement with said magnetizable member for varying said preset magnetic force.

* * * * *